(12) United States Patent
Holguin

(10) Patent No.: US 6,743,880 B2
(45) Date of Patent: Jun. 1, 2004

(54) HYDROPHILIC POLYMERS AND METHODS OF PREPARATION

(75) Inventor: Daniel L. Holguin, Fullerton, CA (US)

(73) Assignee: Avery Denison Corporation, Pasadena, CA (US)

( * ) Notice: Subject to any disclaimer, the term of this patent is extended or adjusted under 35 U.S.C. 154(b) by 0 days.

(21) Appl. No.: 10/133,808

(22) Filed: Apr. 26, 2002

(65) Prior Publication Data

US 2003/0100694 A1 May 29, 2003

Related U.S. Application Data

(63) Continuation-in-part of application No. 09/757,980, filed on Jan. 10, 2001, now Pat. No. 6,653,427, which is a continuation-in-part of application No. 09/540,252, filed on Mar. 31, 2000.

(51) Int. Cl.[7] ............................................... C08F 220/68
(52) U.S. Cl. ..................... 526/320; 526/230; 526/312; 526/317.1; 526/318.4; 526/318.42; 526/319; 526/325; 526/328.5; 526/329.2
(58) Field of Search ................................. 526/320, 230, 526/312, 317.1, 318.4, 318.42, 319, 325, 328.5, 329.2

(56) References Cited

U.S. PATENT DOCUMENTS

| | | |
|---|---|---|
| 2,976,576 A | 3/1961 | Wichterle et al. |
| 3,220,960 A | 11/1965 | Wichterle et al. |
| 3,567,760 A | 3/1971 | Feldman et al. |
| 3,576,760 A | 4/1971 | Gould et al. |
| 3,813,695 A | 6/1974 | Podell, Jr. et al. |
| 3,963,685 A | 6/1976 | Abrahams |
| 4,275,138 A | 6/1981 | Kita et al. |
| 4,303,066 A | 12/1981 | D'Andrea |
| 4,356,288 A | 10/1982 | Lewis et al. |
| 4,379,863 A | 4/1983 | Snyder |
| 4,482,577 A | 11/1984 | Goldstein et al. |
| 4,499,154 A | 2/1985 | James et al. |
| 4,563,184 A | 1/1986 | Korol |
| 4,575,476 A | 3/1986 | Podell et al. |
| 4,593,053 A | 6/1986 | Jevne et al. |
| 4,732,786 A | 3/1988 | Patterson et al. |
| 4,768,523 A | 9/1988 | Cahalan et al. |
| 4,812,549 A | 3/1989 | Muramoto et al. |
| 4,892,787 A | 1/1990 | Kruse et al. |
| 4,935,307 A | 6/1990 | Iqbal et al. |
| 4,994,267 A | 2/1991 | Sablotsky |
| 5,034,154 A | 7/1991 | Yezrielev et al. |
| 5,190,805 A | 3/1993 | Atherton et al. |
| 5,206,071 A | 4/1993 | Atherton et al. |
| 5,225,473 A | 7/1993 | Duan |
| 5,336,208 A | 8/1994 | Rosenbluth et al. |
| 5,478,631 A | 12/1995 | Kawano et al. |
| 5,508,366 A * | 4/1996 | Andrist et al. ............... 526/320 |
| 5,516,865 A | 5/1996 | Urquiola |
| 5,580,565 A | 12/1996 | Tighe et al. |
| 5,665,477 A | 9/1997 | Meathrel et al. |
| 5,672,392 A | 9/1997 | De Clercq et al. |
| 5,695,484 A | 12/1997 | Cox |
| 5,700,585 A | 12/1997 | Lee |
| 5,712,346 A | 1/1998 | Lee |

FOREIGN PATENT DOCUMENTS

| | | |
|---|---|---|
| DE | 19516111 A1 | 11/1996 |
| EP | 024164 A1 | 2/1981 |
| EP | 0716929 A1 | 6/1996 |
| JP | 2-22302 A | 1/1990 |
| WO | WO92/11825 | 7/1992 |
| WO | WO99/06454 | 2/1999 |

OTHER PUBLICATIONS

Polymer International, vol. 36, no. 4, p. 303–308 (Apr. 1995).
Cuang, et al. "Avery Adhesive Test, AAT," Adhesive Age, vol. 40, no. 10, p.18–23 (1997).
E.P. Chang, "Visoelastic Windows of Pressure–Sensitive Adhesives," J. Adhesion, vol. 34, p. 189–200 (1991).
E.P. Chang, "Visoelastic Properties of Pressure–Sensitive Adhesives," J. Adhesion, p. 233–248 (1997).

* cited by examiner

*Primary Examiner*—Tatyana Zalukaeva
(74) *Attorney, Agent, or Firm*—Renner, Kenner, Greive, Bobak, Taylor & Weber

(57) ABSTRACT

The present invention provides a method for the preparation of hydrophilic water insoluble, gel-free copolymers of 2-hydroxyethyl methacrylate and at least one of acrylic acid or methacrylic acid, and 2-hydroxyethyl methacrylate, 4-hydroxybutyl acrylate and acrylic or methacrylic acid, where the copolymers are prepared in a solution of water and alcohol using monomeric 2-hydroxyethyl methacrylate containing ethylene glycol dimethacrylate impurities up to about 0.15% by weight and substantially in the absence of a chain transfer agent. The copolymers are convertible to water soluble copolymers by pH adjustment. The invention also provides a method for the preparation of a copolymer of 2-hydroxyethyl methacrylate and 4-hydroxybutyl acrylate, and a homopolymer of 2-hydroxyethyl methacrylate in a solution of water and either a monoalcohol or a polyhydric alcohol. The polymers are useful in topical skin applications, including use as cosmetic compositions, dermatological compositions, and flexible skin coatings, and as pressure sensitive adhesives.

24 Claims, No Drawings

HYDROPHILIC POLYMERS AND METHODS OF PREPARATION

CROSS REFERENCE TO RELATED APPLICATIONS

The present application is a continuation-in-part of U.S. Ser. No. 09/757,980, filed on Jan. 10, 2001 U.S. Pat. No. 6,563,427, which is a continuation-in-part of U.S. Ser. No. 09/540,252, filed on Mar. 31, 2000, both of which are incorporated herein by reference.

BACKGROUND OF THE INVENTION

The family of synthetic hydrophilic polymers includes polyacrylic acid, polyvinyl pyrrolidone, polyvinyl alcohol, polyacrylamide, poly hydroxybutyl acrylate, and poly 2-hydroxyethyl methacrylate. In this family of synthetic hydrophilic polymers, poly 2-hydroxyethyl methacrylate and poly hydroxybutyl acrylate are water insoluble polymers prepared from a water soluble monomer. The other polymers require crosslinking to form a water insoluble polymer.

2-Hydroxyethyl methacrylate polymers are of interest because of their biocompatibility, as evidenced by excellent performance in animal implant studies. The extensive use of 2-hydroxyethyl methacrylate polymers for contact lenses for the eyes illustrates the non irritating nature of the polymers.

Other than commercial use in contact lenses, 2-hydroxyethyl methacrylate polymers have had limited commercial success, used at low percentages only, because of the nature of the monomer. Industrial grade 2-hydroxyethyl methacrylate monomer contains a small amount of crosslinker impurity, which can cause gel formation during solvent polymerization. The preparation of 2-hydroxyethyl methacrylate polymer, therefore, generally requires the use of very pure and expensive monomer having ethylene glycol dimethacrylate impurities less than 0.035 weight percent, based on the weight of the monomer, or a very extensive and expensive polymerization process.

U.S. Pat. No. 2,976,576 describes the use of poly 2-hydroxyethyl methacrylate resin for contact lenses and body implants.

U.S. Pat. No. 3,220,960 describes the use of poly 2-hydroxyethyl methacrylate resin for contact lenses and body implants.

U.S. Pat. No. 3,567,760 describes the preparation of 2-hydroxyethyl methacrylate copolymers in methanol that are water soluble salts for entrapping drugs, pesticides, flavoring agents, and fragrances.

U.S. Pat. No. 3,963,685 describes the preparation of methanol soluble poly 2-hydroxyethyl methacrylate for wound care dressings using high purity 2-hydroxyethyl methacrylate monomer having not over 0.035 weight percent of alkylene glycol dimethacrylate impurities.

EP 024164A1 describes the preparation of methanol soluble poly 2-hydroxyethyl methacrylate using high purity 2-hydroxyethyl methacrylate monomer.

Polymer International, vol. 36 no. 4, pp.303–308 (April 1995), describes the preparation of dimethylformamide soluble poly 2-hydroxyethyl methacrylate using a chain transfer agent to prevent gellation.

U.S. Pat. No. 4,303,066 describes the use of a plasticized poly 2-hydroxyethyl methacrylate resin prepared from high purity monomer as a non-tacky synthetic film for skin burns, with shortened forming time by adding water to the mixture.

U.S. Pat. No. 4,593,053 describes the use of a plasticized polyvinyl pyrrolidone as a hydrophilic medical type pressure sensitive adhesive for biomedical electrodes and transdermal devices.

WO 92/11825 describes the use of plasticized poly 2-hydroxyethyl methacrylate resin as a hydrophilic medical type pressure sensitive adhesive for a medical device.

U.S. Pat. No. 5,225,473 describes the use of a UV cured plasticized polyvinyl pyrrolidone as a hydrophilic medical type pressure sensitive adhesive for biomedical electrodes and transdermal devices.

U.S. Pat. No. 5,206,071 describes acrylic graft copolymers and water soluble polymers.

EP 0716929A1 describes acrylic graft copolymers and water soluble polymers.

DE 19516111A1 describes water soluble copolymers with crosslinkers.

U.S. Pat. No. 3,813,695 discloses a rubber or latex surgical glove that is laminated with an internal plastic lining of a hydrophilic material.

U.S. Pat. No. 4,575,476 discloses a dipped rubber glove having an outer rubber layer and a lubricating layer formed of a hydrogel polymer bonded thereto to provide a skin-contacting surface of the glove.

BRIEF SUMMARY OF THE INVENTION

In general, the present invention relates to providing a cost-effective method for the preparation of gel-free, hydrophilic polymers, which have utility in topical skin applications, as cosmetic compositions, dermatological compositions, and as skin friendly coatings; as pressure sensitive adhesives; and as precursors for hydrogels.

The present invention provides a method for the preparation of a water insoluble, gel-free copolymer of 2-hydroxyethyl methacrylate and acrylic acid or methacrylic acid substantially in the absence of a chain transfer agent comprising: introducing monomeric 2-hydroxyethyl methacrylate containing ethylene glycol dimethacrylate impurities up to about 0.15% by weight, based on the weight of the monomer, and at least one of acrylic acid or methacrylic acid into a solution of water and alcohol; and copolymerizing the 2-hydroxyethyl methacrylate and the at least one of acrylic acid or methacrylic acid to form a polymerization mixture.

In one embodiment, the monomeric 2-hydroxyethyl methacrylate useful in the inventive method may contain ethylene glycol dimethacrylate impurity in the range of about 0.05% to about 0.1% by weight of the monomer. In another embodiment, the inventive method uses a monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

Hydrophilic pressure sensitive adhesives are provided by adding polyalkylene glycol to the polymerization mixture. Flexible skin coatings are provided by adding a flexiblizing agent to the polymerization mixture.

The present invention also provides a method for the preparation of a hydrophilic, gel-free, water insoluble copolymer of 2-hydroxyethyl methacrylate, 4-hydroxybutyl acrylate and at least one of acrylic acid or methacrylic acid substantially in the absence of a chain transfer agent comprising: introducing monomeric 2-hydroxyethyl methacrylate, monomeric 4-hydroxybutyl acrylate and at least one of acrylic acid or methacrylic acid into a solution of water and alcohol, wherein the monomeric 2-hydroxyethyl methacrylate contains ethylene glycol dimethacrylate impurities up to about 0.15% by weight, based on the weight of the monomer; and copolymerizing the monomeric 2-hydroxyethyl methacrylate, monomeric 4-hydroxybutyl acrylate and at least one of acrylic acid or methacrylic acid to form a polymerization mixture.

In another embodiment, the monomeric 2-hydroxyethyl methacrylate useful in the inventive method contain ethylene glycol dimethacrylate impurity in the range of about 0.05% to about 0.1% by weight of the monomer. In another embodiment, the inventive method uses a monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

Hydrophilic pressure sensitive adhesives are provided by adding polyalkylene glycol to the polymerization mixture. Flexible skin coatings are provided by adding a flexiblizing agent to the polymerization mixture.

The present invention also provides a method for the preparation of a substantially monoalcohol-free, gel-free, water insoluble, hydrophilic copolymer of 2-hydroxyethyl methacrylate and 4-hydroxybutyl acrylate substantially in the absence of a chain transfer agent comprising: introducing monomeric 2-hydroxyethyl methacrylate containing ethylene glycol dimethacrylate impurities up to about 0.15% by weight, based on the weight of the monomer, and monomeric 4-hydroxybutyl acrylate into a solution of water and a monoalcohol; copolymerizing the monomeric 2-hydroxyethyl methacrylate and the 4-hydroxybutyl acrylate to form a polymerization mixture; leaching the copolymer of 2-hydroxyethyl methacrylate and 4-hydroxybutyl acrylate to substantially remove residual monomer; and substantially replacing the monoalcohol with a polyhydric alcohol.

In another embodiment, the monomeric 2-hydroxyethyl methacrylate that is useful in the inventive method may contain ethylene glycol dimethacrylate impurity in the range of about 0.05% to about 0.1% by weight of the monomer. In another embodiment, the inventive method uses a monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

Flexible skin coatings are provided by removing the water after the leaching and replacing steps.

The invention further provides a method for the preparation of a substantially monoalcohol-free, gel-free, water insoluble, hydrophilic copolymer of 2-hydroxyethyl methacrylate and 4-hydroxybutyl acrylate substantially in the absence of a chain transfer agent comprising: introducing monomeric 2-hydroxyethyl methacrylate containing ethylene glycol dimethacrylate impurities up to about 0.15% by weight, based on the weight of the monomer, and monomeric 4-hydroxybutyl acrylate into a solution of water and polyhydric alcohol; and copolymerizing the monomeric 2-hydroxyethyl methacrylate and the 4-hydroxybutyl acrylate to form a polymerization mixture.

In another embodiment, the monomeric 2-hydroxyethyl methacrylate that is useful in the inventive method may contain ethylene glycol dimethacrylate impurity in the range of about 0.05% to about 0.1% by weight of the monomer. In another embodiment, the inventive method uses a monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

Flexible skin coatings are provided by substantially removing the water from the polymerization mixture.

The invention further provides a method for the preparation of a substantially monoalcohol-free, gel-free, water insoluble, hydrophilic homopolymer of 2-hydroxyethyl methacrylate substantially in the absence of a chain transfer agent comprising: introducing monomeric 2-hydroxyethyl methacrylate containing ethylene glycol dimethacrylate impurities up to about 0.15% by weight, based on the weight of the monomer, into a solution of water and a monoalcohol; polymerizing the 2-hydroxyethyl methacrylate to form a polymerization mixture; leaching the homopolymer of 2-hydroxyethyl methacrylate to substantially remove residual monomer; and substantially replacing the monoalcohol with a polyhydric alcohol.

In another embodiment, the monomeric 2-hydroxyethyl methacrylate that is useful in the inventive method may contain ethylene glycol dimethacrylate impurity in the range of about 0.05% to about 0.1% by weight of the monomer. In another embodiment, the inventive method uses a monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

Flexible skin coatings are provided by substantially removing the water from the polymer after the leaching and replacing steps.

The present invention further provides a method for the preparation of substantially gel-free, water insoluble, hydrophilic homopolymer of 2-hydroxyethyl methacrylate substantially in the absence of a chain transfer agent comprising: introducing monomeric 2-hydroxyethyl methacrylate containing ethylene glycol dimethacrylate impurities up to about 0.15% by weight, based on the weight of the monomer, into a solution of water and polyhydric alcohol; and polymerizing the 2-hydroxyethyl methacrylate to form a polymerization mixture.

As such, this invention relates to the method of preparing gel-free, hydrophilic, water insoluble homopolymers and copolymers, and gel-free, hydrophilic water soluble copolymers that are suitable in the formulation of topical compositions for application to human skin and hair, such as cosmetic compositions and dermatological compositions, and to their use as pressure sensitive adhesives and flexible coatings.

DETAILED DESCRIPTION OF THE INVENTION

The present invention involves processes for the preparation of gel-free, water insoluble copolymers that can be subsequently converted to gel-free, hydrophilic, water soluble copolymers by pH adjustment. The copolymer products of the present invention can be prepared from an inexpensive industrial or technical grade 2-hydroxyethyl methacrylate monomer source that contains low levels of ethylene glycol dimethacrylate impurity.

The gel-free, water insoluble copolymers of the present invention can be subjected to a leaching process to substantially remove residual unreacted monomer from the copolymerization mixture to achieve a copolymer product having even lower residual monomer content. While the copolymers of the present invention have many uses, the copolymer products having low residual monomer content are especially useful in the formulation of cosmetic products for application to the skin and hair, and of dermatological products for use in skin and hair care applications.

The term "gel free" as used in the specification is intended to be synonymous with the phrases "soluble in alcohol" or "insoluble in water." The presence or absence of gel in the polymer products of the present invention can be determined by visually inspecting the polymerization mixture for the presence of particulates. Optionally, a thin film of the polymer product can be poured and visually inspected for particulates. A polymer product containing no particulate matter upon visual inspection is considered to be "gel-free."

In one embodiment, the present invention provides a method for the preparation of a gel-free, water insoluble copolymer of 2-hydroxyethyl methacrylate and acrylic acid or methacrylic acid substantially in the absence of a chain transfer agent. The method of producing the gel-free copolymer includes introducing monomeric 2-hydroxyethyl methacrylate containing ethylene glycol dimethacrylate impurities up to about 0.15% by weight of the monomer, and at least one of acrylic acid or methacrylic acid into a solution of water and alcohol. The monomeric 2-hydroxyethyl methacrylate and monomeric acrylic acid and/or methacrylic acid are polymerized to form a polymerization mixture containing a copolymer of 2-hydroxyethyl methacrylate and acrylic acid and/or methacrylic acid.

The method of preparing the gel-free, water insoluble copolymer of 2-hydroxyethyl methacrylate and acrylic acid and/or methacrylic acid can utilize monomeric 2-hydroxyethyl methacrylate containing ethylene glycol dimethacrylate impurities in the range of about 0.05% to about 0.1%, by weight of the 2-hydroxyethyl methacrylate monomer.

The method of preparing the gel-free, water insoluble copolymer of 2-hydroxyethyl methacrylate and acrylic acid and/or methacrylic acid may also utilize monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

The method of the present invention, therefore, provides for the cost effective preparation of a gel-free 2-hydroxyethyl methacrylate copolymers using industrial grade 2-hydroxyethyl methacrylate monomer. A 2-hydroxyethyl methacrylate monomer that is particularly suitable for use in the method of the present invention is available from Mitsubishi Rayon, Japan. This 2-hydroxyethyl methacrylate monomer contains less than 0.15% by weight of ethylene glycol dimethacrylate impurity, based on the weight of the monomer. The controlled level of impurities in the 2-hydroxyethyl methacrylate monomer results in a gel-free polymer, without the need for using a very expensive, ultra-pure 2-hydroxyethyl methacrylate monomer source.

2-Hydroxyethyl methacrylate monomer suitable for use in the method of the present invention may also be made by blending industrial grade 2-hydroxyethyl methacrylate monomer from various sources to provide the desired level of impurities. Although less economical, 2-hydroxyethyl methacrylate monomer suitable for use in the method of the present invention may also be made by adding specified amounts of impurities to a higher purity 2-hydroxyethyl methacrylate monomer, to control the properties desired.

As described above, the copolymer of 2-hydroxyethyl methacrylate and acrylic or methacrylic acid is prepared in a solution of alcohol and water. The alcohol used in the inventive method may include $C_1$–$C_4$ lower alcohols. Preferably, the alcohol used in the copolymerization of 2-hydroxyethyl methacrylate and acrylic acid and/or methacrylic acid, according to the inventive method, is ethanol.

The method for the preparation of a gel-free, water insoluble copolymer of 2-hydroxyethyl methacrylate and methacrylic or acrylic acid occurs substantially in the absence of a chain transfer agent. Polymerization is induced by free radical initiation using a suitable free radical polymerization initiator. The initiator preferably should be soluble in alcohol, water and the monomer mixture. The initiator is added to the alcohol/water solution containing the mixture of the monomeric 2-hydroxyethyl methacrylate and acrylic or methacrylic acid in an amount effective to initiate copolymerization. Suitable initiators include dissociative initiators and redox initiators. Suitable dissociative initiators that may be used in the present invention include, but are not limited to, persulfates such as ammonium persulfate, potassium persulfate and sodium persulfate, hydrogen peroxide, tert-butyl hydroperoxide, and azo compounds such as 4,4'-azobis(4-cyanovaleric acid). Redox initiators include, but are not limited to, persulfates with bisulfite, such as sodium persulfate with sodium metabisulfite, hydrogen peroxide with ferrous ion, sulfite ion, bisulfite ion or ascorbic acid, and hydroperoxides with sulfoxylates, such as tert-butyl hydroperoxide with sodium formaldehyde sulfoxylate.

The gel-free, water insoluble copolymer of 2-hydroxyethyl methacrylate and acrylic or methacrylic acid may be subjected to a conventional leaching process to remove unreacted, residual monomer from the polymerization mixture. Typically, a desired amount of water is added to the polymerization mixture to precipitate the copolymer product. The effluent forms on the surface of the copolymer product and is easily decanted off. Thereafter, the copolymer product may be redissolved with a suitable diluent and then precipitated again. The diluents that can be used to redissolve the copolymer product preferably include, but are not limited to, lower alcohols, alkylene glycols and polyalkylene glycols. Preferably, ethanol and polypropylene glycol are used to redissolve the copolymer product during the leaching process.

The gel-free, water insoluble, leached copolymer of 2-hydroxyethyl methacrylate and acrylic or methacrylic acid is converted to a hydrophilic, gel-free, water soluble copolymer by pH adjustment with a suitable base. According to the present invention, the water insoluble copolymer can be converted to a water soluble copolymer by adjusting the pH of the copolymer to a pH of greater than about 4.5. Preferably, the pH of the copolymer is adjusted to a pH in the range of about 5.5 to about 7.5. Suitable bases that can be used to adjust the pH of the copolymerization mixture include, but are not limited to, hydroxides such as ammonium hydroxide, potassium hydroxide, sodium hydroxide and alcohol amines, such as triethanolamine.

In another embodiment, the present invention provides a method for the preparation of a pressure sensitive adhesive formulation. The method includes preparing a gel-free, water insoluble copolymer of 2-hydroxyethyl methacrylate and acrylic or methacrylic acid. The method utilizes monomeric 2-hydroxyethyl methacrylate containing ethylene glycol dimethacrylate impurity up to about 0.15 weight %, based on the weight of the monomer, to prepare a copolymer of 2-hydroxyethyl methacrylate and acrylic or methacrylic acid. The monomeric 2-hydroxyethyl methacrylate that is useful in the inventive method may contain ethylene glycol dimethacrylate impurity in the range of about 0.05% to about 0.1% by weight of the monomer. Furthermore, the 2-hydroxyethyl methacrylate contains alkylene glycol methacrylate impurities in the range of about 3%, based on the weight of the monomer. Preferably, the alkylene glycol impurities are selected from the group consisting of ethylene glycol dimethacrylate, diethylene glycol monomethacrylate, methacrylic acid and mixtures thereof, in a total amount of no more than about 3% by weight of monomer.

The copolymer is then leached as described above. A polyalkylene glycol is then added to the copolymerization mixture, and the alcohol and water is substantially removed from the polymerization mixture to form a hydrophilic pressure sensitive adhesive. Suitable polyalkylene glycols that can be added to the copolymerization mixture to form the pressure sensitive adhesive include polyethylene glycol, polypropylene glycol and copolymers of polyethylene glycol and polypropylene glycol. Preferably, the polyalkylene glycol used to prepare the pressure sensitive adhesive is polyethylene glycol. The polyalkylene glycol, such as polyethylene glycol, can be added to the copolymerization mixture in an amount ranging from about 40% to about 70% by weight, based on the weight of the copolymer and the polyalkylene glycol. Furthermore, the pH of the copolymer product can be adjusted, as described above, to render the copolymer product water soluble prior to the addition of the polyalkylene to the polymerization mixture. The hydrophilic pressure sensitive adhesives formed by this method have utility in many label and tape applications, and is particularly suitable for medical applications.

In a further embodiment, the present invention provides a method for the preparation of a flexible hydrophilic coating including a gel-free copolymer of 2-hydroxyethyl methacrylate and one of acrylic or methacrylic acid, produced substantially in the absence of a chain transfer agent. The method comprises introducing monomeric 2-hydroxyethyl methacrylate containing ethylene glycol dimethacrylate impurities up to about 0.15 weight %, based on the weight of the monomer into a solution of alcohol and water. The monomers are copolymerized to form a polymerization mixture. The polymerization mixture is then leached to remove residual monomer. A suitable flexiblizing agent is added to the copolymerization mixture to impart a flexibility property to the copolymer, and then the alcohol and water is removed to form a hydrophilic, flexible coating. Suitable flexiblizing agents include, for example, alkylene glycols and glycerin. Preferably, the flexiblizing agents that are added to the copolymerization mixture to form the flexible skin coating are propylene glycol and glycerin. The flexiblizing agent should be added to the copolymerization mixture in amount sufficient to impart a desired level of flexibility to the copolymer. Preferably, the flexiblizing agent is added to the polymerization mixture in an amount ranging from about 10% to about 50% by weight of the polymer, most preferably the flexiblizing agent is added to the polymerization mixture in amount of about 25%, by weight of the polymer.

The monomeric 2-hydroxyethyl methacrylate that is useful in the inventive method may contain ethylene glycol dimethacrylate impurity in the range of about 0.05% to about 0.1% by weight of the monomer. Furthermore, the 2-hydroxyethyl methacrylate contains alkylene glycol methacrylate impurities in the range of about 3%, based on the weight of the monomer. Preferably, the alkylene glycol impurities are selected from the group consisting of ethylene glycol dimethacrylate, diethylene glycol monomethacrylate, methacrylic acid and mixtures thereof, in a total amount of no more than about 3% by weight of monomer. Furthermore, the pH of the copolymer product can be adjusted, as described above, to render the copolymer product water soluble prior to the addition of the flexibilizing agent to the polymerization mixture. The flexible hydrophilic coating formed by this method has utility in skin-friendly applications in which a high Moisture Vapor Transmission Rate (MVTR) is needed together with protective, skin barrier properties. The coating is also suitable for printable coatings, such as inkjet coatings for paper, plastic film, and the like.

In another embodiment, the present invention provides a method for the preparation of a gel free, water insoluble copolymer of 2-hydroxyethyl methacrylate, 4-hydroxybutyl acrylate and acrylic and/or methacrylic acid. The method includes introducing monomeric 2-hydroxyethyl methacrylate containing up to about 0.15 weight % of ethylene glycol dimethacrylate impurity, based on the weight of the monomer, monomeric 4-hydroxybutyl acrylate and monomeric acrylic and/or methacrylic acid into a solution of alcohol and water, and copolymerizing these monomers to form a polymerization mixture. The alcohol is selected from lower alcohols, and is preferably selected from one of methanol and ethanol. More preferably, the lower alcohol used is ethanol.

The method of a preparing the gel free, water insoluble copolymer of 2-hydroxyethyl methacrylate, 4-hydroxybutyl acrylate and acrylic and/or methacrylic acid may include using monomeric 2-hydroxyethyl methacrylate containing 0.05 to 0.1% by weight of ethylene glycol dimethacrylate impurities, based on the weight of the monomer.

The method of preparing the gel free, water insoluble copolymer of 2-hydroxyethyl methacrylate, 4-hydroxybutyl acrylate and acrylic and/or methacrylic acid may include using monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

A 2-hydroxyethyl methacrylate monomer that is particularly suitable for use in the preparation of a copolymer of 2-hydroxyethyl methacrylate, 4-hydroxybutyl acrylate and acrylic and/or methacrylic acid is available from Mitsubishi Rayon, Japan. The Mitsubishi 2-hydroxyethyl methacrylate monomer contains less than 0.15% by weight of ethylene glycol dimethacrylate impurity, based on the weight of the monomer. The controlled level of impurities in the 2-hydroxyethyl methacrylate monomer permits the preparation of the gel-free polymer, without the need for using a very expensive, ultra-pure 2-hydroxyethyl methacrylate monomer source.

The method for the preparation of a gel-free, water insoluble copolymer of 2-hydroxyethyl methacrylate, 4-hydroxybutyl acrylate and methacrylic or acrylic acid occurs substantially in the absence of a chain transfer agent. Polymerization is induced by free radical initiation using a suitable free radical polymerization initiator. The initiator is added to the alcohol/water solution containing the mixture of the monomeric 2-hydroxyethyl methacrylate, 4-hydroxybutyl acrylate and acrylic or methacrylic acid in an amount effective to initiate copolymerization. The initiator preferably should be soluble in alcohol, water and the monomer mixture. Suitable initiators for the copolymerization of the monomeric 2-hydroxyethyl methacrylate, 4-hydroxybutyl acrylate and acrylic or methacrylic acid that are soluble in water include, but are not limited to, dissociative initiators and redox initiators. Suitable dissociative initiators that may be used in the present invention include, but are not limited to, persulfates such as ammonium persulfate, potassium persulfate and sodium persulfate, hydrogen peroxide, tert-butyl hydroperoxide, and azo compounds such as 4,4'-azobis(4-cyanovaleric acid). Redox initiators include, but are not limited to, persulfates with bisulfite, such as sodium persulfate with sodium metabisulfite, hydrogen peroxide with ferrous ion, sulfite ion, bisulfite ion or ascorbic acid, and hydroperoxides with sulfoxylates, such as tert-butyl hydroperoxide with sodium formaldehyde sulfoxylate.

The gel-free, water insoluble copolymer of 2-hydroxyethyl methacrylate, 4-hydroxybutyl acrylate and acrylic or methacrylic acid may be subjected to a conventional leaching process to substantially remove unreacted, residual monomer from the polymerization mixture. Typically, a desired amount of water is added to the polymerization mixture to precipitate the copolymer product. The effluent forms on the surface of the copolymer product and is decanted off. Thereafter, the copolymer product is redissolved with a suitable diluent, followed by further precipitation and decanting. The diluents that can be used to redissolve the copolymer product preferably include, but are not limited to, lower alcohols, alkylene glycols and polyalkylene glycols. Preferably, ethanol and polypropylene glycol are used to redissolve the copolymer product during the leaching process.

The gel-free, water insoluble, leached copolymer of 2-hydroxyethyl methacrylate, 4-hydroxybutyl acrylate and acrylic or methacrylic acid can be converted to a hydrophilic, gel-free, water soluble copolymer by pH adjustment with a suitable base. According to the present invention, the pH of the copolymerization mixture need only be adjusted to a pH at which the water insoluble copolymer is converted to a water soluble copolymer. Preferably, the water insoluble copolymer can be converted to a water soluble copolymer by adjusting the pH of the copolymer to a pH of greater than about 4.5. More preferably, the pH of the copolymer can be adjusted to a pH in the range of about 5.5 to about 7.5. The pH adjustment of the copolymer can be achieved through the addition of a suitable base to a water/alcohol solution containing the copolymer or to a water/alkylene glycol solution containing the copolymer. Alternatively, the pH of the copolymer can be adjusted by redissolving the precipitated copolymer with a suitable base. Suitable bases that can be used to adjust the pH of the copolymer include, but are not limited to, hydroxides such as ammonium hydroxide, potassium hydroxide and sodium hydroxide, and alcohol amines, such as triethanolamine.

In one embodiment, the present invention provides a method for the preparation of a pressure sensitive adhesive formulation. The method includes preparing a gel-free, water insoluble copolymer of 2-hydroxyethyl methacrylate, 4-hydroxybutyl acrylate and acrylic or methacrylic acid. The method utilizes monomeric 2-hydroxyethyl methacrylate containing ethylene glycol dimethacrylate impurities up to about 0.15 weight %, based on the weight of the monomer. The monomeric 2-hydroxyethyl methacrylate that is useful in the inventive method may contain ethylene glycol dimethacrylate impurity in the range of about 0.05% to about 0.1% by weight of the monomer. Furthermore, the 2-hydroxyethyl methacrylate contains alkylene glycol methacrylate impurities in the range of about 3%, based on the weight of the monomer. Preferably, the alkylene glycol impurities are selected from the group consisting of ethylene glycol dimethacrylate, diethylene glycol monomethacrylate, methacrylic acid and mixtures thereof, in a total amount of no more than about 3% by weight of monomer. The monomeric 2-hydroxyethyl methacrylate, 4-hydroxybutyl acrylate and acrylic or methacrylic acid are copolymerized to form a polymerization mixture.

A polyalkylene glycol is then added to the copolymerization mixture and the alcohol and water is substantially removed to form a hydrophilic pressure sensitive adhesive. Suitable polyalkylene glycols that can be added to the copolymer to form the pressure sensitive adhesive include polyethylene glycol, polypropylene glycol and copolymers of polyethylene glycol and polypropylene glycol. Preferably, the polyalkylene glycol used to prepare the pressure sensitive adhesive is polyethylene glycol. The polyalkylene glycol, such as polyethylene glycol, can be added to the copolymerization mixture in an amount ranging from about 40% to about 70% by weight, based on the weight of the copolymer and the polyalkylene glycol. Prior to the addition of the polyalkylene glycol to the polymerization mixture, the copolymer product can be leached, as described above, to substantially remove residual monomer. Furthermore, the pH of the copolymer product can be adjusted to render the copolymer product water soluble before addition of the polyalkylene glycol to the polymerization mixture. The hydrophilic pressure sensitive adhesives formed by this method have utility in many label and tape applications, and is particularly suitable for medical applications.

In a further embodiment, the present invention provides a method for the preparation of a flexible hydrophilic coating comprising a gel-free copolymer of 2-hydroxyethyl methacrylate, 4-hydroxybutyl acrylate and one of acrylic or methacrylic acid, produced substantially in the absence of a chain transfer agent. The method comprises introducing monomeric 2-hydroxyethyl methacrylate containing ethylene glycol dimethacrylate impurities up to about 0.15 weight %, based on the weight of the monomer, monomeric 4-hydroxybutyl acrylate and monomeric acrylic and/or methacrylic acid into a solution of alcohol and water. The monomeric 2-hydroxyethyl methacrylate that is useful in the inventive method may contain ethylene glycol dimethacrylate impurity in the range of about 0.05% to about 0.1% by weight of the monomer. Furthermore, the 2-hydroxyethyl methacrylate contains alkylene glycol methacrylate impurities in the range of about 3%, based on the weight of the monomer. Preferably, the alkylene glycol impurities are selected from the group consisting of ethylene glycol dimethacrylate, diethylene glycol monomethacrylate, methacrylic acid and mixtures thereof, in a total amount of no more than about 3% by weight of monomer.

The monomers are copolymerized to form a polymerization mixture. A suitable flexiblizing agent is added to the copolymerization mixture to impart a flexibility property to the copolymer, and the alcohol and water is removed to for a hydrophilic, flexible coating. Suitable flexiblizing agents include, for example, alkylene glycols and glycerin. Preferably, the flexiblizing agents that are added to the copolymerization mixture to form the flexible skin coating are propylene glycol and glycerin. The flexiblizing agent should be added to the copolymerization mixture in amount sufficient to impart a desired level of flexibility to the copolymer. Preferably, the flexiblizing agent is added to the polymerization mixture in an amount ranging from about 10% to about 50% by weight of the polymer, preferably the flexiblizing agent is added to the polymerization mixture in amount of about 25%, by weight of the polymer The flexible hydrophilic coating formed by this method has utility in skin-friendly applications in which a high Moisture Vapor Transmission Rate (MVTR) is needed together with protective, skin barrier properties. The coating is also suitable for printable coatings, such as inkjet coatings for paper, plastic film, and the like.

The copolymer of 2-hydroxyethyl methacrylate, 4-hydroxybutyl acrylate and acrylic and/or methacrylic acid is a hydrophilic copolymer that, before pH adjustment, is insoluble in water and does not require crosslinking for water resistance. In addition, the copolymer of 2-hydroxyethyl methacrylate, 4-hydroxybutyl acrylate and methacrylic acid is flexible enough to form a flexible coating or film for medical and skin care or skin protection applications without the need for the addition of glycerin. The flexible coating comprising the copolymer of 2-hydroxyethyl methacrylate, 4-hydroxybutyl acrylate and methacrylic acid is also useful as a rubber or latex glove coating, with particular usefulness in wet-donning applications. Rubber or latex gloves require the ability of donning, that is, the ability to slide a glove on and off the surface of the skin with minimal friction. The copolymer of 2-hydroxyethyl methacrylate, 4-hydroxybutyl acrylate and methacrylic acid provides a flexible, non-tacky glove coating that allows the donning, wet or dry, of the rubber or latex glove with minimal blocking and without undue friction or clinging.

The present invention, in one embodiment, provides a gel-free, hydrophilic copolymer of 2-hydroxyethyl methacrylate, 4-hydroxybutyl acrylate and methacrylic acid that does not to be plasticized. The copolymer of 2-hydroxyethyl methacrylate, 4-hydroxybutyl acrylate and acrylic and/or methacrylic acid, before pH adjustment, is a water-insoluble, water-absorbing, amphiphilic, elastic, abrasion resistant and has improved mechanical properties. It should be noted, however, that while the copolymer of 2-hydroxyethyl methacrylate, 4-hydroxybutyl acrylate and methacrylic acid alone can be flexible enough to form a flexible skin coating, a desired flexiblizing agent, for example, glycerin or an alkyl glycol can be added to the copolymer to further enhance the performance as a skin coating.

A method for the preparation of hydrophilic, gel-free, water insoluble copolymer of 2-hydroxyethyl methacrylate and 4-hydroxybutyl acrylate substantially in the absence of a chain transfer agent is also included in the present invention. According to this embodiment, the copolymer of 2-hydroxyethyl methacrylate and 4-hydroxybutyl acrylate is substantially free of monoalcohol. The method includes introducing monomeric 2-hydroxyethyl methacrylate containing ethylene glycol dimethacrylate impurities up to about 0.15% by weight of the monomer and monomeric 4-hydroxybutyl acrylate into a solution of water and a monoalcohol. The monomeric 2-hydroxyethyl methacrylate and the 4-hydroxybutyl acrylate are then copolymerized in the solution of water and the monoalcohol to form a polymerization mixture. The copolymer is leached to remove residual unreacted monomer. The monoalcohol present in the leached copolymer product of 2-hydroxyethyl methacrylate and 4-hydroxybutyl acrylate is substantially replaced by redissolving the copolymer in a polyhydric alcohol, followed by further leaching and decanting, to produce a substantially monoalcohol-free copolymer of 2-hydroxyethyl methacrylate and 4-hydroxybutyl acrylate.

As used in the specification, the term "monoalcohol" refers to a monohydric alcohol. Without limitation, the monoalcohol used in the polymerization process is preferably selected from monohydric $C_1$–$C_4$ alkyl alcohols. More preferably, the monoalcohol used in the copolymerization of 2-hydroxyethyl methacrylate and 4-hydroxybutyl acrylate is selected from methanol and ethanol. The term "polyhydric alcohol" refers to an alcohol having more than one hydroxyl group and, is intended to encompass both dihydric alcohols, which have two hydroxyl groups, and alcohols having more than two hydroxyl groups.

The method of preparing the gel-free, water insoluble copolymer of 2-hydroxyethyl methacrylate and 4-hydroxybutyl acrylate, in another embodiment, can utilize monomeric 2-hydroxyethyl methacrylate containing ethylene glycol dimethacrylate impurities in the range of about 0.05% to about 0.1%, by weight of the 2-hydroxyethyl methacrylate monomer.

The method of preparing the gel-free, water insoluble copolymer of 2-hydroxyethyl methacrylate and 4-hydroxybutyl acrylate may also utilize monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

The method of forming the gel-free, water insoluble copolymer of 2-hydroxyethyl methacrylate and 4-hydroxybutyl acrylate employs the use of an industrial grade 2-hydroxyethyl methacrylate monomer. A 2-hydroxyethyl methacrylate industrial grade monomer that is particularly suitable for use in the method is available from Mitsubishi Rayon, Japan. This 2-hydroxyethyl methacrylate monomer contains less than about 0.15% by weight of ethylene glycol dimethacrylate impurity, based on the weight of the monomer.

2-Hydroxyethyl methacrylate monomer suitable for use in the method of preparing a copolymer of 2-hydroxyethyl methacrylate and 4-hydroxybutyl acrylate may also be made by blending industrial grade 2-hydroxyethyl methacrylate monomer from various sources to provide the desired level of impurities. Although less economical, 2-hydroxyethyl methacrylate monomer suitable for use in the method of the present invention may also be made by adding specified amounts of impurities to a higher purity 2-hydroxyethyl methacrylate monomer, to control the properties desired.

The preparation of a gel-free, water insoluble copolymer of 2-hydroxyethyl methacrylate and 4-hydroxybutyl acrylate occurs substantially in the absence of a chain transfer agent. Polymerization is induced by free radical initiation using a suitable free radical polymerization initiator. The initiator preferably should be soluble in alcohol, water and the monomer mixture. The initiator is added to the alcohol/water solution containing the mixture of the monomeric 2-hydroxyethyl methacrylate and 4-hydroxybutyl acrylate in an amount effective to initiate copolymerization. Suitable initiators include dissociative initiators and redox initiators. Suitable dissociative initiators that may be used in the present invention include, but are not limited to, persulfates such as ammonium persulfate, potassium persulfate and sodium persulfate, hydrogen peroxide, tert-butyl hydroperoxide, and azo compounds such as 4,4'-azobis(4-cyanovaleric acid). Redox initiators include, but are not limited to, persulfates with bisulfite, such as sodium persulfate with sodium metabisulfite, hydrogen peroxide with ferrous ion, sulfite ion, bisulfite ion or ascorbic acid, and hydroperoxides with sulfoxylates, such as tert-butyl hydroperoxide with sodium formaldehyde sulfoxylate.

As described above, the gel-free, water insoluble copolymer of 2-hydroxyethyl methacrylate and 4-hydroxybutyl acrylate may be subjected to a conventional leaching process to substantially remove unreacted, residual monomer from the polymerization mixture. Typically, a desired amount of water is added to the polymerization mixture to precipitate the copolymer product. The effluent forms on the surface of the copolymer product and is easily decanted off. Thereafter, the copolymer product is redissolved with a suitable diluent, and the redissolved copolymer may be subjected to further precipitation and decanting. Preferably, polyhydric alcohols are used to redissolve the copolymer product. Suitable polyhydric alcohols that can be used to redissolve the copolymer product include, but are not limited to, alkylene glycols, alkyl ethers of alkylene glycols, diols, glycerin and alkyl esters of glycerin. By redissolving the copolymer product in a polyhydric alcohol, the monoalcohol present in the copolymer product is substantially replaced by the polyhydric alcohol to produce a substantially monoalcohol free copolymer of 2-hydroxyethyl methacrylate and 4-hydroxybutyl acrylate.

The preferred alkylene glycols that can be used include, but are not limited to ethylene glycol and propylene glycol, with propylene glycol being more preferred. Where alkyl ethers of alkylene glycols are used to redissolve the copolymer product, the alkyl ethers of alkylene glycols may be selected from ethylene glycol monomethyl ether, ethylene glycol monoethyl ether, propylene glycol monomethyl ether and propylene glycol monoethyl ether. Furthermore, diols may be used to redissolve the copolymer product of 2-hydroxyethyl methacrylate and 4-hydroxybutyl acrylate. Suitable diols that may be utilized include, but are not limited to, 1,3-butanediol, 1,4-butanediol, 2-methyl-2,4-pentanediol, 2,5-hexanediol and 2,4-heptanediol. Glycerin and alkyl esters of glycerin may be utilized to redissolve the copolymer product of 2-hydroxyethyl methacrylate and 4-hydroxybutyl acrylate. If utilized, the alkyl esters of glycerin may include glycerin monolaurate, glycerin monooleate and glycerin monostearate. Preferably, polypropylene glycol or glycerin are used to redissolve the copolymer product.

The invention also includes a method for the preparation of substantially monoalcohol-free, gel-free, water insoluble, hydrophilic copolymer of 2-hydroxyethyl methacrylate and 4-hydroxybutyl acrylate substantially in the absence of a chain transfer agent comprising. The method, according this embodiment, includes introducing monomeric 2-hydroxyethyl methacrylate containing ethylene glycol dimethacrylate impurities up to about 0.15% by weight, based on the weight of the monomer, and monomeric 4-hydroxybutyl acrylate into a solution of water and polyhydric alcohol. The monomeric 2-hydroxyethyl methacrylate and the 4-hydroxybutyl acrylate are copolymerized in the solution of water and polyhydric alcohol to form a polymerization mixture containing the copolymer.

The polyhydric alcohol in which the copolymerization of 2-hydroxethyl methacrylate and 4-hydroxybutyl acrylate occurs includes, but is not limited to, alkylene glycols, alkyl ethers of alkylene glycols, diols, glycerin and alkyl esters of glycerin. The copolymer may be leached, preferably with water, to remove residual monomer. The polyhydric alcohol may be replaced by a monoalcohol by redissolving the copolymer in a monoalcohol, followed by leaching and decanting.

The present invention includes a method for the preparation of a pressure sensitive adhesive including the copolymer of 2-hydroxyethyl methacrylate and 4-hydroxybutyl acrylate. The method includes preparing a gel-free, water insoluble copolymer of 2-hydroxyethyl methacrylate and 4-hydroxybutyl acrylate. The method utilizes monomeric 2-hydroxyethyl methacrylate containing ethylene glycol dimethacrylate impurity up to about 0.15 weight %, based on the weight of the monomer, to prepare a copolymer of 2-hydroxyethyl methacrylate and 4-hydroxybutyl acrylate. The copolymer is then leached as described above. A polyalkylene glycol is then added to the copolymerization mixture, and the alcohol and water is substantially removed from the polymerization mixture to form a hydrophilic pressure sensitive adhesive. Suitable polyalkylene glycols that can be added to the copolymerization mixture to form the pressure sensitive adhesive include polyethylene glycol, polypropylene glycol and copolymers of polyethylene glycol and polypropylene glycol. Preferably, the polyalkylene glycol used to prepare the pressure sensitive adhesive is polyethylene glycol. The polyalkylene glycol, such as polyethylene glycol, can be added to the copolymerization mixture in an amount ranging from about 40% to about 70% by weight, based on the weight of the copolymer and the polyalkylene glycol. The hydrophilic pressure sensitive adhesives formed by this method have utility in many label and tape applications, and is particularly suitable for medical applications.

The method of preparing the pressure sensitive adhesive including the gel-free, water insoluble copolymer of 2-hydroxyethyl methacrylate and 4-hydroxybutyl acrylate can also utilize monomeric 2-hydroxyethyl methacrylate containing ethylene glycol dimethacrylate impurities in the range of about 0.05% to about 0.1%, by weight of the 2-hydroxyethyl methacrylate monomer.

The method of preparing the pressure sensitive adhesive including the gel-free, water insoluble copolymer of 2-hydroxyethyl methacrylate and 4-hydroxybutyl acrylate may further utilize monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

The present invention also provides a method for the preparation of a flexible hydrophilic coating including a gel-free, water insoluble copolymer of 2-hydroxyethyl methacrylate and 4-hydroxybutyl acrylate, produced substantially in the absence of a chain transfer agent. The method comprises introducing monomeric 2-hydroxyethyl methacrylate containing ethylene glycol dimethacrylate impurities up to about 0.15 weight %, based on the weight of the monomer into a solution of alcohol and water. The monomers are copolymerized to form a polymerization mixture. The polymerization mixture is then leached to remove residual monomer. A suitable flexiblizing agent is added to the copolymerization mixture to impart a flexibility property to the copolymer, and then the alcohol and water is removed to form a hydrophilic, flexible coating. Suitable flexiblizing agents include, for example, alkylene glycols and glycerin. Preferably, the flexiblizing agents that are added to the copolymerization mixture to form the flexible skin coating are propylene glycol and glycerin. The flexiblizing agent should be added to the copolymerization mixture in amount sufficient to impart a desired flexiblizing property to the copolymer. Preferably, the flexiblizing agent is added to the polymerization mixture in an amount ranging from about 10% to about 50% by weight of the polymer, most preferably the flexiblizing agent is added to the polymerization mixture in amount of about 25%, by weight of the polymer. It should be noted, however, that while the copolymer of 2-hydroxyethyl methacrylate, and 4-hydroxybutyl acrylate alone can be flexible enough to form a flexible skin coating, a desired flexiblizing agent, for example, glycerin or an alkylene glycol can be added to the copolymer to further enhance the performance as a skin coating.

A method for the preparation of substantially monoalcohol-free, gel-free, water insoluble, hydrophilic homopolymer of 2-hydroxyethyl methacrylate substantially in the absence of a chain transfer agent is also provided. The method comprises introducing monomeric 2-hydroxyethyl methacrylate containing ethylene glycol dimethacrylate impurities up to about 0.15% by weight, based on the weight of the monomer, into a solution of water and a monoalcohol. The monomeric 2-hydroxyethyl methacrylate is polymerized to form a polymerization mixture containing the homopolymer. The homopolymer of 2-hydroxyethyl methacrylate may be leached to substantially remove residual monomer, followed by substantially replacing the monoalcohol with a polyhydric alcohol.

The same polyhydric alcohols used to redissolve the copolymer of 2-hydroxyethyl methacrylate and 4-hydroxybutyl acrylate and to substantially replace the monoalcohol in that copolymer can be used to redissolve the homopolymer of 2-hydroxyethyl methacrylate and to substantially replace the monoalcohol present in the homopolymer.

The method of preparing the gel-free, hydrophilic, water insoluble polymer of 2-hydroxyethyl methacrylate, in another embodiment, can utilize monomeric 2-hydroxyethyl methacrylate containing ethylene glycol dimethacrylate impurities in the range of about 0.05% to about 0.1%, by weight of the 2-hydroxyethyl methacrylate monomer.

The method of preparing the gel-free, hydrophilic, water insoluble polymer of 2-hydroxyethyl methacrylate may also utilize monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

The method of forming the gel-free, water insoluble polymer of 2-hydroxyethyl methacrylate employs the use of an industrial grade 2-hydroxyethyl methacrylate monomer. A 2-hydroxyethyl methacrylate industrial grade monomer that is particularly suitable for use in the method is available from Mitsubishi Rayon, Japan. This 2-hydroxyethyl methacrylate monomer contains less than 0.15% by weight of ethylene glycol dimethacrylate impurity, based on the weight of the monomer.

2-Hydroxyethyl methacrylate monomer suitable for use in the method of preparing a homopolymer of 2-hydroxyethyl methacrylate may also be made by blending industrial grade 2-hydroxyethyl methacrylate monomer from various sources to provide the desired level of impurities. Although less economical, 2-hydroxyethyl methacrylate monomer suitable for use in the method of the present invention may also be made by adding specified amounts of impurities to a higher purity 2-hydroxyethyl methacrylate monomer, to control the properties desired.

A method for the preparation of gel-free, hydrophilic homopolymer of 2-hydroxyethyl methacrylate substantially in the absence of a chain transfer agent is also included in the present invention. The method includes introducing monomeric 2-hydroxyethyl methacrylate containing ethylene glycol dimethacrylate impurities up to about 0.15% by weight into a solution of water and a polyhydric alcohol. The 2-hydroxyethyl methacrylate is then polymerized to form a polymerization mixture containing the homopolymer.

The method of preparing the gel-free, hydrophilic, water insoluble polymer of 2-hydroxyethyl methacrylate, in another embodiment, can utilize monomeric 2-hydroxyethyl methacrylate containing ethylene glycol dimethacrylate impurities in the range of about 0.05% to about 0.1%, by weight of the 2-hydroxyethyl methacrylate monomer.

The method of preparing the gel-free, hydrophilic, water insoluble polymer of 2-hydroxyethyl methacrylate may also utilize monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

The method of forming the gel-free, water insoluble polymer of 2-hydroxyethyl methacrylate employs the use of an industrial grade 2-hydroxyethyl methacrylate monomer. A 2-hydroxyethyl methacrylate industrial grade monomer that is particularly suitable for use in the method is available from Mitsubishi Rayon, Japan. This 2-hydroxyethyl methacrylate monomer contains less than 0.15% by weight of ethylene glycol dimethacrylate impurity, based on the weight of the monomer.

2-Hydroxyethyl methacrylate monomer suitable for use in the method of preparing a homopolymer of 2-hydroxyethyl methacrylate may also be made by blending industrial grade 2-hydroxyethyl methacrylate monomer from various sources to provide the desired level of impurities. Although less economical, 2-hydroxyethyl methacrylate monomer suitable for use in the method of the present invention may also be made by adding specified amounts of impurities to a higher purity 2-hydroxyethyl methacrylate monomer, to control the properties desired.

The polyhydric alcohol in which the copolymerization of 2-hydroxethyl methacrylate and 4-hydroxybutyl acrylate occurs includes, but is not limited to, alkylene glycols, alkyl ethers of alkylene glycols, diols, glycerin and alkyl esters of glycerin.

The preparation of a gel-free, water insoluble homopolymer of 2-hydroxyethyl methacrylate occurs substantially in the absence of a chain transfer agent. Polymerization is induced by free radical initiation using a suitable free radical polymerization initiator. The initiator preferably should be soluble in alcohol, water and the monomer. The initiator is added to the alcohol/water solution containing the monomeric 2-hydroxyethyl methacrylate in an amount effective to initiate polymerization. Suitable initiators include dissociative initiators and redox initiators. Suitable dissociative initiators that may be used in the present invention include, but are not limited to, persulfates such as ammonium persulfate, potassium persulfate and sodium persulfate, hydrogen peroxide, tert-butyl hydroperoxide, and azo compounds such as 4,4'-azobis(4-cyanovaleric acid). Redox initiators include, but are not limited to, persulfates with bisulfite, such as sodium persulfate with sodium metabisulfite, hydrogen peroxide with ferrous ion, sulfite ion, bisulfite ion or ascorbic acid, and hydroperoxides with sulfoxylates, such as tert-butyl hydroperoxide with sodium formaldehyde sulfoxylate.

The gel-free, water insoluble homopolymer of 2-hydroxyethyl methacrylate may subjected to a conventional leaching process to substantially remove unreacted, residual monomer from the polymerization mixture. Typically, a desired amount of water is added to the polymerization mixture to precipitate the polymer product. The effluent forms on the surface of the polymer product and is easily decanted off. Thereafter, the polymer product is redissolved with a suitable diluent, and the redissolved polymer can be subjected to further precipitation and decanting. The diluents that can be used to redissolve the polymer product preferably include, but are not limited to, lower alcohols, alkylene glycols and polyalkylene glycols. Preferably, ethanol and polypropylene glycol are used to redissolve the polymer product during the leaching process. Furthermore, the polyhydric alcohol can be substantially replaced with a monohydric alcohol by redissolving the homopolymer in a monohydric alcohol, followed by further leaching and decanting to drive off the polyhydric alcohol, thus resulting in a copolymer product containing the monohydric alcohol.

The present invention includes a method for the preparation of a pressure sensitive adhesive including the homopolymer of 2-hydroxyethyl methacrylate. The method includes preparing a gel-free, water insoluble homopolymer of 2-hydroxyethyl methacrylate. The method utilizes monomeric 2-hydroxyethyl methacrylate containing ethylene glycol dimethacrylate impurity up to about 0.15 weight %, based on the weight of the monomer, to prepare a homopolymer of 2-hydroxyethyl methacrylate. The homopolymer is then leached as described above to substantially remove residual monomer. A polyalkylene glycol is then added to the polymerization mixture, and the alcohol and water is substantially removed from the polymerization mixture to form a hydrophilic pressure sensitive adhesive. Suitable polyalkylene glycols that can be added to the polymerization mixture to form the pressure sensitive adhesive include polyethylene glycol, polypropylene glycol and copolymers of polyethylene glycol and polypropylene glycol. Preferably, the polyalkylene glycol used to prepare the pressure sensitive adhesive is polyethylene glycol. The polyalkylene glycol, such as polyethylene glycol, can be added to the polymerization mixture in an amount ranging from about 40% to about 70% by weight, based on the weight of the copolymer and the polyalkylene glycol. The hydrophilic pressure sensitive adhesives formed by this method have utility in many label and tape applications, and is particularly suitable for medical applications.

The present invention also provides a method for the preparation of a flexible hydrophilic coating including a gel-free, water insoluble homopolymer of 2-hydroxyethyl methacrylate, produced substantially in the absence of a chain transfer agent. The method comprises introducing monomeric 2-hydroxyethyl methacrylate containing ethylene glycol dimethacrylate impurities up to about 0.15 weight %, based on the weight of the monomer into a solution of alcohol and water. The monomer is polymerized to form a polymerization mixture. The polymerization mixture is then leached to substantially remove residual monomer. A suitable flexiblizing agent is added to the copolymerization mixture to impart a flexibility property to the homopolymer, and then the alcohol and water is removed to form a hydrophilic, flexible coating. Suitable flexiblizing agents include, for example, alkylene glycols and glycerin. Preferably, the flexiblizing agents that are added to the polymerization mixture to form the flexible skin coating are propylene glycol and glycerin. The flexiblizing agent should be added to the polymerization mixture in amount sufficient to impart a desired flexiblizing property to the homopolymer. Preferably, the flexiblizing agent is added to the polymerization mixture in an amount ranging from about 10% to about 50% by weight of the homopolymer, most preferably the flexiblizing agent is added to the polymerization mixture in amount of about 25%, by weight of the polymer.

The copolymer product of 2-hydroxyethyl methacrylate and acrylic and/or methacrylic acid, the copolymer product of 2-hydroxyethyl methacrylate, 4-hydroxybutyl acrylate and acrylic and/or methacrylic acid, the copolymer of 2-hydroxyethyl methacrylate and 4-hydroxybutyl acrylate, and the homopolymer of 2-hydroxyethyl methacrylate may further contain up to about 10 weight percent of an additional monomer, based on the weight of the polymeric product. More preferably, the polymeric product may contain from about 2 to about 4 weight percent of the additional monomer. The inclusion of up to about 10 weight percent of the additional monomer increases the cohesive strength of the polymer product, while still maintaining pressure sensitive adhesive properties, skin coating properties, and water resistance. Useful monomers that may be added to the polymer products of the present invention include, for example, alkyl acrylates, alkyl methacrylates, hydroxyalkyl acrylates, hydroxyalkyl methacrylates, fluorinated alkyl acrylates, including 1H, 1H-triflouroethyl acrylate, 1H, 1H-heptaflourobutyl acrylate and 1H, 1H-pentadecaflourooctyl acrylate, fluorinated alkyl methacrylates including 1H, 1H-triflouroethyl methacrylate, 1H, 1H-heptaflourobutyl methacrylate and 1H, 1H-pentadecaflourooctyl methacrylate, N-vinyl lactam, dimethylaminoethyl acrylate, methylene chloride quaternary salt of dimethylaminoethyl acrylate, diethylaminoethyl acrylate, methylene chloride quaternary salt of diethylaminoethyl acrylate, dimethylaminoethyl methacrylate, methylene chloride quaternary salt of dimethylaminoethyl methacrylate, diethylaminoethyl methacrylate, methylene chloride quaternary salt of diethylaminoethyl methacrylate, vinyl acetate and styrene monomers. The alkyl component of the above monomers is preferably a $C_1$–$C_{17}$ alkyl group.

The copolymer of 2-hydroxyethyl methacrylate and acrylic and/or methacylic acid, or the copolymer of 2-hydroxyethyl methacrylate, 4-hydroxybutyl acrylate, and acrylic and/or methacrylic acid can utilize other polymerizable acid monomers besides acrylic acid and methacrylic acid. Non-limiting examples of other polymerizable acid monomers include, but are not limited to, b-carboxyethyl acrylate, crotonic acid, maleic acid, fumaric acid, and itaconic acid.

In general, the copolymer of 2-hydroxyethyl methacrylate and acrylic and/or methacrylic acid, the copolymer of 2-hydroxyethyl methacrylate, 4-hydroxybutyl acrylate and acrylic and/or methacrylic acid, the copolymer of 2-hydroxyethyl methacrylate and 4-hydroxybutyl acrylate, and the homopolymer of 2-hydroxyethyl methacrylate can be utilized in topical skin formulations, including cosmetic compositions, dermatological preparations and compositions, skin coatings or barriers. Some useful applications of these polymers include use as sprayable carriers for topical application of drugs to the skin. These polymers may also be a component of a cream, including water in oil emulsions and oil in water emulsions; lotions, which are suspensions in water or oil; ointments, which are solutions in petroleum or polyethylene glycol; or aerosols, which are sprayable solutions in water/alcohol and gels.

The polymers may also be a component of a transdermal drug delivery system. Specifically, the polymers can be used as a carrier or vehicle to deliver an effective amount of a pharmacologically active agent (drug) transdermally. In this embodiment, the polymers may be loaded with an effective amount of a pharmacologically active agent and locally placed on the surface of the skin. The transdermal drug delivery system can also include, as known in the art, skin permeation enhancers to facilitate the transdermal delivery of the pharmacologically active agent. The polymers can perform a dual function as a carrier of a pharmacologically active agent and a protective coating or skin barrier.

The polymers can also be sprayed onto the skin before the application of adhesive-coated bandages, tapes, or other adhesive-coated medical devices to prevent irritation of sensitive skin.

The polymers can be used as an elastomeric medical film. Preferably, the polymers can be coated onto a substrate, such as a release liner and dried. The polymers will be self cross-linking with heat treatment. Preferably, the polymers will be self cross-linking by heat treating at a temperature in the range of about 70° C. to about 150° C., more preferably in a temperature range of about 70° C. to about 125° C. The elastomeric medical film can be used directly over a wound on the skin to provide a dressing or barrier. The elastomeric film is soft and pliable, and easily conforms to the contours of human skin.

The polymers may also be included in sun block and sunscreen lotions, creams, sprays and as a carrier or vehicle of ultra-violet (UV) light absorbers, such as aminobenzoic acid, benzophenone-8 and benzophenone-4.

The polymers can be used as a carrier for cosmetic products. Cosmetic compositions including the polymers are easy to apply to and remove from the surface of human skin, are non-greasy, and non-occlusive. Like skin, the polymers are hydrophilic, amphiphilic and elastic.

The polymers can also be included as a component of a nasal spray or other mucus membrane drug delivery systems, as a carrier for a pharmacologically active agent, such as a pharmaceutical. Using a mucus membrane drug delivery system is a potential benefit over ingestion of pills, tablets or capsules, or repeated injections of pharmacologically active agents, because these traditional methods have initially high concentrations of the pharmacologically active agent, which may be toxic or cause side effects to the target organ or surrounding structures. As time passes, the concentration of the pharmacologically active agent diminishes and another dosage is required to maintain the pharmacologically effective level. Utilizing a mucus membrane drug delivery system including the polymers as a carrier for a pharmacologically active agent may permit the delivery of an effective amount of a pharmacologically active agent and maintenance of the pharmacologically effective level over longer periods of time.

The polymers can be blended with a polyalkylene glycol, such as polyethylene glycol, to form a pressure sensitive adhesive. The pressure sensitive adhesive can be coated onto a substrate, such as a release liner, in the formation of a pressure sensitive product. The pressure sensitive adhesive products can be used as a bandage, tape, wound dressing, surgical drape, ostomy site dressing and the like.

In another embodiment, the invention provides a method of coating a substrate comprising applying to a substrate the polymerization mixture any of the polymers that are prepared in a solution of water and alcohol, and further comprising adding a polyalkylene glycol to the polymerization mixture prior to the removing of the alcohol and water, and thereafter forming a hydrophilic pressure sensitive adhesive upon removing the alcohol and water from the polymerization mixture. The polyalkylene glycol to be added to the polymerization mixture includes, but is not limited to, polyethylene glycol, polypropylene glycol, copolymers of ethylene glycol and propylene glycol and mixtures thereof.

The polymers of the present invention may be applied to various substrates as described below by any conventional means known in the art such as die coating, roll coating, reverse roll coating, gravure coating, reverse gravure coating, offset gravure coating, Mayer rod or wire wound rod coating, spraying, brushing, and the like. The polymers of the present invention may be heated or cooled to facilitate the coating process to provide a desired coating of the polymer on the substrate.

Any of the polymer products produced in accordance with the present invention can be dried. The dried polymer may then be pulverized into a powder, or sprayed dried into a powder.

The amount of the polymer that is to applied to a substrate may be varied depending upon the characteristics of the substrate, the characteristics desired to be imparted to the substrate, and the particular characteristics of the polymers and copolymers. For economic reasons, it is normally desired to apply the lowest amount of coating to obtain the desired result. Typically, the applied coating weights may, depending on the substrate and intended use, range from about 0.1 to about 100 grams/meter$^2$. For pressure sensitive adhesive applications, the amount is preferably in the range of about 15 grams/meter$^2$ to about 45 grams/meter$^2$. For hydrophilic coating and ink jet coating applications, the amount is preferably from about 1 gram/meter$^2$ to about 25 grams/meter$^2$.

The substrate which is used in the present invention may be any substrate material such as paper, or polymeric films in the form of sheets and strips, and the like. Preferred types of paper include semi-gloss paper and high gloss paper. In one embodiment, the substrate is a polymeric film. In a preferred embodiment, the substrate is a polymeric film formed from a thermoplastic material. In a more preferred embodiment, the substrate is a polymeric film selected from the group consisting of polystyrene, a polyester, and a polyolefin such as polyethylene or polypropylene.

Composites of the present invention may be prepared in various forms including webs which may be in roll form and which can thereafter be cut or slit into strips or sheets of desired dimensions.

The polymers prepared in accordance with the methods of the present invention are suitable for the preparation of and use as elastomeric films, pressure sensitive adhesives, coatings, precursors ro hydrogels, compositions for topical applications to the skin such as, creams, lotions, ointments, gels, aerosols, sprays, cosmetic compositions, dermatological preparations and composotions, deodorants, and insect repellants.

As mentioned above, the unique combination of characteristics makes the polymers suitable for use in medical elastomeric films, bandages, tapes, wound care dressings, surgical drapes, ostomy site dressings, as a carrier for transdermal drug delivery systems, and as a carrier for mucus membrane drug delivery systems. These medical products can be loaded with a pharmacologically active agent. Typical pharmacologically active agents include, but are not limited to, corticosteroids, anti-acne agents such as retinoic acid and benzoyl peroxide, anti-infectives such as erythromycin, tetracycline, and clindamycin, anti-fungals such as tolnaftate, undecylenic acid, nystatin, clotrimazole, and fluconazole, antioxidants such as butylated hydroxytoluene, t-butylhydroquinone, tocopherol, surfactants such as sodium lauryl sulfate, UV absorbers such as aminobenzoic acid, benzphenon-8, and benzophenone-4, humectants such as propylene glycol, glycerin, polyethylene glycol, and butylene glycol, alpha hydroxy acids, and emollients such as castor oil, mineral oil, petroleum cetyl palmitate, cetyl alcohol, and stearyl alcohol.

The following examples illustrate the methods of preparation of the hydrophilic homopolymers and copolymers of the present invention. It should be noted that the examples are intended for illustrative purposes only, and are not intended to limit the scope of the invention in any manner.

EXAMPLE 1

A copolymer of comprising 67.5 weight % 2-hydroxyethyl methacrylate, 30 weight % 4-hydroxybutyl acrylate and 2.5 weight % methacrylic acid was prepared according to the following recipe and procedure:

| Recipe | |
|---|---|
| Reactor Charge | |
| 2-Hydroxyethyl Methacrylate (Mitsubishi) | 270 g |
| 4-Hydroxybutyl acrylate | 120 g |
| Methacrylic acid | 10 g |
| Ethanol | 373.2 g |
| Deionized Water | 373.2 g |
| Initiator Charge | |
| Deionized Water | 10 g |
| Sodium Persulfate (0.5%) | 2 g |
| Cook-Off Initiator #1 | |
| Deionized Water | 5 g |
| Ethanol | 5 g |
| Sodium Persulfate | 0.4 g |
| Cook off Initiator #2 | |
| Deionized Water | 5 g |
| Ethanol | 5 g |
| Sodium Persulfate | 0.4 g |
| Cook off Initiator #3 | |
| Deionized Water | 5 g |
| Ethanol | 5 g |
| Sodium Metabisulfite | 0.4 g |
| Total | 1189.6 g |

Polymerization Procedure

1. The Reactor Charge was weighed out into a flask and introduced into a reaction kettle.
2. The Reactor Charge was heated with a 80° C. jacket and with $N_2$ purging of the Reactor Charge.
3. The initiator charge was added to the heated and $N_2$ purged Reactor Charge.
4. After about 10 minutes, the polymerization was started for a three hour period, while maintaining a jacket temperature of about 83° C.
5. After about three hours of polymerization, Cook Off Initiator #1 was added into the reaction kettle.
6. One hour after adding Cook Off Initiator #1, Cook Off Initiator #2 was added to the reaction kettle.
7. One hour after adding Cook Off Initiator #2, Cook Off Initiator #3 was added to the reaction kettle.
8. After an additional hour of heating, the reaction kettle was cooled.

The water insoluble copolymer prepared in Example 1 was subjected to a leaching process to remove residual unreacted monomer. The leaching process is described below.

Leaching Process 1096 grams of polymer solution was transferred to the leaching vessel and the leaching process to remove unreacted monomer is described below.

| | |
|---|---|
| First Leach | |
| Water added to precipitate polymer | 2200 g |
| Decant off effluent | 1708.8 g |
| Ethanol to redissolve | 160 g |
| Second Leach | |
| Water added to precipitate polymer | 1100 g |
| Decant off effluent | 989.4 g |
| Ethanol to redissolve | 120 g |
| Third Leach | |
| Water added to precipitate polymer | 1100 g |
| Decant off effluent | 1366.5 g |
| Ethanol to redissolve | 140 g |

After completion of the leaching process of the copolymer product of Example 1, the pH of the leached copolymer was adjusted with 4 grams of a 30% ammonium hydroxide solution. The copolymer product was diluted to 5% total solids content (TSC) with water. By visual inspection, the pH adjusted copolymer product appeared slightly hazy in solution. The pH of the diluted copolymer was further adjusted by the addition of 2 grams of 30% by weight ammonium hydroxide solution. The copolymer product was again diluted to 5% TSC with water. The pH of the copolymer product was measured to be 6.6 and, upon visual inspection, the copolymer product appeared clear in solution.

The leached and pH adjusted water soluble copolymer product synthesized in Example No. 1, above, exhibited the following properties:

| | |
|---|---|
| Viscosity, cPs | 864 |
| % Solids content | 20.9% |
| % Ethanol | 15.9% |
| % Water | 63.2% |
| Residual monomer | |
| 2-Hydroxyethyl Methacrylate | <15 ppm |
| 4-Hydroxybutyl Acrylate | <10 ppm |
| Methacrylic Acid | <0.01% |

The presence of any gel formation in the copolymer product was determined by visually inspecting the polymerization mixture or a poured thin film of the copolymer product for any particulate. The appearance of the copolymer product in this example was determined utilizing a visual test looking at the clarity of a poured thin film of the copolymer solution.

The percent solids in the copolymer product was measured by accurately weighing a small aluminum dish, then accurately weighing about 1 gram of wet copolymer sample. The aluminum dish with the sample was dried under an infrared lamp for about 15 minutes. The aluminum dish with the dried sample was cooled and then accurately reweighed. The weight of the dried sample divided by the wet sample multiplied by 100 is the percent total solids in the sample.

The viscosity of the copolymer product was measured under ambient conditions (23–25° C.) with a Brookfield LV Viscometer using an appropriate spindle and speed for the measured viscosity. The viscosity units are centipoise, cPs.

The protocols described hereinabove that were used to measure and evaluate the appearance, percent solids and viscosity of the copolymer product of Example No. 1 apply to all of the below described inventive polymer examples produced according to the present invention, and the comparative examples, unless specifically indicated. The polymerization procedure described above for Example 1, was used for Example Nos. 2–6, 10 and 11 and Comparative Example Nos. 7–9, unless otherwise indicated.

EXAMPLE 2

A copolymer of comprising 97.5 weight % 2-hydroxyethyl methacrylate and 2.5 weight % methacrylic acid was prepared according to the following recipe:

| Recipe | |
|---|---|
| Reactor Charge | |
| 2-Hydroxyethyl Methacrylate (Mitsubishi) | 292.5 g |
| Methacrylic acid | 7.5 g |
| Ethanol | 280 g |
| Deionized Water | 280 g |
| Initiator Charge | |
| Deionized Water | 10 g |
| Sodium Persulfate (0.5%) | 1.5 g |
| Cook-Off Initiator #1 | |
| Deionized Water | 5 g |
| Ethanol | 5 g |
| Sodium Persulfate | 0.3 g |
| Cook off Initiator #2 | |
| Deionized Water | 5 g |
| Ethanol | 5 g |
| Sodium Persulfate | 0.3 g |
| Cook off Initiator #3 | |
| Deionized Water | 5 g |
| Ethanol | 5 g |
| Sodium Metabisulfite | 0.3 g |
| Total | 902.4 g |

The water insoluble copolymer of Example 2 was subjected to a leaching process to remove the residual unreacted monomer. The leaching process is described below.

Leaching Process 755 grams of polymer solution was transferred to the leaching vessel and the polymer was subjected to the leaching process to remove unreacted monomer, as described below.

| First Leach | |
|---|---|
| Water added to precipitate polymer | 1510 g |
| Decant off effluent | 1207.7 g |
| Ethanol to redissolve | 120 g |
| Second Leach | |
| Water added to precipitate polymer | 755 g |
| Decant off effluent | 986.2 g |
| Ethanol to redissolve | 90 g |
| Third Leach | |
| Water added to precipitate polymer | 755 g |
| Decant off effluent | 832.5 g |
| Ethanol to redissolve | 75 g |

After completion of the leaching of the copolymer product of Example 2, the leached copolymer was pH adjusted with 4 grams of a 30% ammonium hydroxide solution and 96 grams of deionized water. The pH of the copolymer product was measured to be 6.4. The copolymer was diluted to 5% total solids content with water and, upon visual inspection, the copolymer product appeared clear in solution.

The leached and pH adjusted copolymer product synthesized in Example No. 2, above, exhibited the following properties:

| | |
|---|---|
| Viscosity, cPs | 12,140 |
| % Solids content | 23.7% |
| % Ethanol | 10.3% |
| % Water | 66% |
| Residual monomers | |
| 2-Hydroxyethyl Methacrylate | <15 ppm |
| Methacrylic Acid | <0.01% |

EXAMPLE 3

A copolymer comprising 97.5 weight % 2-hydroxyethyl methacrylate and 2.5 weight % methacrylic acid was prepared according to the following recipe:

| Reactor Charge | |
|---|---|
| 2-Hydroxyethyl Methacrylate (Mitsubishi) | 292.5 g |
| Methacrylic acid | 7.5 g |
| Ethanol | 280 g |
| Deionized Water | 280 g |
| Initiator Charge | |
| Deionized Water | 10 g |
| Sodium Persulfate (0.5%) | 1.5 g |
| Cook-Off Initiator #1 | |
| Deionized Water | 5 g |
| Ethanol | 5 g |
| Sodium Persulfate | 0.3 g |
| Cook off Initiator #2 | |
| Deionized Water | 5 g |
| Ethanol | 5 g |
| Sodium Persulfate | 0.3 g |
| Cook off Initiator #3 | |
| Deionized Water | 5 g |
| Ethanol | 5 g |
| Sodium Metabisulfite | 0.3 g |
| Total | 902.4 g |

The water insoluble copolymer of Example 3 was subjected to a leaching process to remove residual unreacted monomer. According to this example, the copolymer product was redissolved in propylene glycol instead of ethanol. The leaching process is described below.

Leaching Process 800 grams of polymer solution was transferred to the leaching vessel and the polymer product was subjected to the leaching process to remove unreacted monomer, as described below.

| First Leach | |
|---|---|
| Water added to precipitate polymer | 1600 g |
| Decant off effluent | 1397 g |
| Propylene glycol to redissolve | 165 g |
| Second Leach | |
| Water added to precipitate polymer | 800 g |
| Decant off effluent | 1132 g |
| Propylene glycol to redissolve | 140 g |
| Third Leach | |
| Water added to precipitate polymer | 800 g |
| Decant off effluent | 996 g |
| Propylene glycol to redissolve | 121 g |

After completion of the leaching of the copolymer product of Example 3, the leached copolymer was pH adjusted with 3 grams of a 30% ammonium hydroxide solution in 300 grams of deionized water. The pH of the copolymer product was measured to be 5.8. The copolymer was diluted to 5% total solids content with water and, upon visual inspection, the copolymer product appeared clear in solution. The leached and pH adjusted copolymer product synthesized in Example No. 3, above, exhibited the following properties:

| | |
|---|---|
| Viscosity, cPs | 61,600 |
| % Solids content | 25.5% |
| % Water | 64.2% |
| % Propylene glycol | 10.3% |
| % Ethanol | 0.7% |
| Residual monomers | |
| 2-Hydroxyethyl Methacrylate | <0.59% |
| Methacrylic Acid | <0.01% |

EXAMPLE 4

A copolymer of comprising 67.5 weight % 2-hydroxyethyl methacrylate, 30 weight % 4-hydroxybutyl acrylate and 2.5 weight % methacrylic acid was prepared according to the following recipe:

| Recipe | |
|---|---|
| Reactor Charge | |
| 2-Hydroxyethyl Methacrylate (Mitsubishi) | 337.5 g |
| 4-Hydroxybutyl acrylate | 150 g |
| Methacrylic acid | 12.5 g |
| Ethanol | 466.5 g |
| Deionized Water | 466.5 g |
| Initiator Charge | |
| Deionized Water | 12.5 g |
| Sodium Persulfate (0.5%) | 2.5 g |
| Cook-Off Initiator #1 | |
| Deionized Water | 6.25 g |
| Ethanol | 6.25 g |
| Sodium Persulfate | 0.5 g |
| Cook off Initiator #2 | |
| Deionized Water | 6.25 g |
| Ethanol | 6.25 g |
| Sodium Persulfate | 0.5 g |
| Cook off Initiator #3 | |
| Deionized Water | 6.25 g |
| Ethanol | 6.25 g |
| Sodium Metabisulfite | 0.5 g |
| Total | 1487 g |

Leaching Process 1000 grams of polymer solution was transferred to the leaching vessel and the polymer product was subjected to a leaching process to remove unreacted monomer, as described below.

| First Leach | |
|---|---|
| Water added to precipitate polymer | 2000 g |
| Decant off effluent | 1225 g |
| Ethanol to redissolve | 145 g |
| Second Leach | |
| Water added to precipitate polymer | 1000 g |
| Decant off effluent | 1189 g |
| Ethanol to redissolve | 145 g |
| Third Leach | |
| Water added to precipitate polymer | 1000 g |
| Decant off effluent | 1024 g |
| Ethanol to redissolve | 145 g |
| Fourth Leach | |
| Water added to precipitate polymer | 1000 g |
| Decant off effluent | 1093 g |

After completion of the leaching of the copolymer product of Example 4, the copolymer product was both redissolved and the pH adjusted in a solution of 4 grams of a 30% ammonium hydroxide solution in 150 grams of deionized water. The copolymer product was diluted to 5% total solids content (TSC) with water. Upon visual inspection the copolymer product appeared slightly hazy. The pH of the diluted copolymer was further adjusted by the addition of 2.4 grams of 30% by weight ammonium hydroxide solution. The copolymer product was again diluted to 5% TSC with water. The pH was the copolymer product was measured to be 7.6 and, upon visual inspection, the copolymer product appeared clear in solution. The leached and pH adjusted copolymer product synthesized in Example No. 4, above, exhibited the following properties:

| | |
|---|---|
| Viscosity, cPs | 1904 |
| % Solids content | 18.4% |
| % Ethanol | 4% |
| % Water | 81.2% |
| Residual monomers | |
| 2-Hydroxyethyl Methacrylate | <15 ppm |
| 4-Hydroxybutyl acrylate | <20 ppm |
| Methacrylic Acid | <0.01% |

EXAMPLE 5

329 grams of polymer product prepared in accordance with Example 4 was transferred to the leaching vessel and the polymer product was subjected to a leaching process to remove unreacted monomer, as described below.

| LEACHING PROCESS | |
|---|---|
| First Leach | |
| Water added to precipitate polymer | 660 g |
| Decant off effluent | 472.6 g |
| Ethanol to redissolve | 50 g |
| Second Leach | |
| Water added to precipitate polymer | 330 g |
| Decant off effluent | 349.6 g |
| Ethanol to redissolve | 50 g |
| Third Leach | |
| Water added to precipitate polymer | 330 g |
| Decant off effluent | 407.6 g |

After completion of the leaching of the copolymer product, the copolymer product was both redissolved and pH adjusted with a solution containing 1.7 grams of triethanolamine in 50 grams of deionized water and. Upon visual inspection, the copolymer product appeared hazy in solution. The copolymer product was diluted to 5% TSC with water. Upon visual inspection, the copolymer product appeared milky in solution. The pH of the diluted copolymer product was adjusted with an additional 2.1 grams of triethanolamine. The pH of the copolymer was measured as 6.3. The copolymer product was added diluted to 5% TSC and, upon visual inspection, the copolymer was clear in solution. The leached and pH adjusted copolymer product of Example No. 5 exhibited the following properties:

| | |
|---|---|
| Viscosity, cPs | 6480 |
| % Solids content | 20.3% |
| % Ethanol | 8.3% |
| % Water | 71.4% |
| Residual monomers | |
| 2-Hydroxyethyl Methacrylate | <30 ppm |
| 4-Hydroxybutyl acrylate | <20 ppm |
| methacrylic acid | 0.1% |

EXAMPLE 6

A copolymer comprising 60 weight % 2-hydroxyethyl methacrylate, 30 weight % 4-hydroxybutyl acrylate and 10 weight % methacrylic acid was prepared according to the following recipe:

| Recipe | |
|---|---|
| Reactor Charge | |
| 2-Hydroxyethyl Methacrylate (Mitsubishi) | 240 g |
| 4-Hydroxybutyl acrylate | 120 g |
| Methacrylic acid | 40 g |
| Ethanol | 373.2 g |
| Deionized Water | 373.2 g |
| Initiator Charge | |
| Deionized Water | 10 g |
| Sodium Persulfate (0.5%) | 2 g |

| -continued | |
|---|---|
| Recipe | |
| Cook-Off Initiator #1 | |
| Deionized Water | 5 g |
| Ethanol | 5 g |
| Sodium Persulfate | 0.4 g |
| Cook off Initiator #2 | |
| Deionized Water | 5 g |
| Ethanol | 5 g |
| Sodium Persulfate | 0.4 g |
| Cook off Initiator #3 | |
| Deionized Water | 5 g |
| Ethanol | 5 g |
| Sodium Metabisulfite | 0.4 g |
| Total | 1189.6 g |

The water insoluble was subjected to a leaching process to remove residual unreacted monomer. The leaching process is described below.

Leaching Process 1078 grams of copolymer solution of Example 6 was transferred to the leaching vessel and copolymer was subjected to a leaching process to remove unreacted monomer, as described below.

| First Leach | |
|---|---|
| Water to precipitate polymer | 2000 g |
| Decant off effluent | 1515.4 g |
| Ethanol to redissolve | 150 g |
| Second Leach | |
| Water to precipitate polymer | 1000 g |
| Decant off effluent | 924.8 g |
| Ethanol to redissolve | 150 g |
| Third Leach | |
| Water to precipitate polymer | 1000 g |
| Decant off effluent | 1184.5 g |
| Ethanol to redissolve | 150 g |

After completion of the leaching of the copolymer product of Example 6, the pH of the leached copolymer was adjusted with 4 grams of a 30% ammonium hydroxide solution. Upon visual inspection, the copolymer product appeared clear in solution. The copolymer product was then diluted to 5% TSC with water. Upon visual inspection, the copolymer product precipitated out of solution. The pH of the diluted copolymer product was adjusted with 6 grams of a 30% ammonium hydroxide solution. The pH of the was measured as 6.5. The copolymer product was again diluted to 5% TSC and, upon visual inspection, the copolymer was clear in solution. The leached and pH adjusted copolymer product synthesized in Example No. 6, above, exhibited the following properties:

| | |
|---|---|
| Viscosity, cPs | 2920 |
| % Solids content | 19.9% |
| % Ethanol | 20.5% |
| % Water | 59.6% |

-continued

| Residual monomers | |
|---|---|
| 2-Hydroxyethyl Methacrylate | <30 ppm |
| 4-Hydroxybutyl acrylate | <20 ppm |
| Methacrylic Acid | <0.01% |

COMPARATIVE EXAMPLE 7

A copolymer of 67.5 weight % 2-hydroxyethyl methacrylate, 30 weight % 4-hydroxybutyl acrylate and 2.5 weight % methacrylic acid was prepared according to the following recipe. The copolymer of Comparative Example 7 was prepared with a 2-hydroxyethyl methacrylate monomer source containing 0.17 weight % ethylene glycol dimethacrylate impurity, which monomer source is commercially available from Rohm & Haas under the tradename Rocryl 400:

| Recipe | |
|---|---|
| Reactor Charge | |
| 2-Hydroxyethyl Methacrylate (Rohm & Haas) | 270 g |
| 4-Hydroxybutyl acrylate | 120 g |
| Methacrylic acid | 10 g |
| Ethanol | 373.2 g |
| Deionized Water | 373.2 g |
| Initiator Charge | |
| Deionized Water | 10 g |
| Sodium Persulfate (0.5%) | 2 g |
| Cook-Off Initiator #1 | |
| Deionized Water | 5 g |
| Ethanol | 5 g |
| Sodium Persulfate | 0.4 g |
| Cook off Initiator #2 | |
| Deionized Water | 5 g |
| Ethanol | 5 g |
| Sodium Persulfate | 0.4 g |
| Cook off Initiator #3 | |
| Deionized Water | 5 g |
| Ethanol | 5 g |
| Sodium Metabisulfite | 0.4 g |
| Total | 1189.6 g |

The copolymer of Comparative Example 7 formed a hydrogel during the polymerization process. Without being bound to any particular theory, the inventor surmises that the formation of the hydrogel can be attributed to the higher level of ethylene glycol dimethacrylate present in the 2-hydroxyethyl methacrylate monomer source from Rohm & Haas.

COMPARATIVE EXAMPLE 8

A homopolymer of 2-hydroxyethyl methacrylate was prepared according to the following recipe:

| Recipe | |
|---|---|
| Reactor Charge | |
| 2-Hydroxyethyl Methacrylate (Mitsubishi) | 233.4 g |
| Ethanol | 225.5 g |
| Deionized Water | 225.5 g |

-continued

| Recipe | |
|---|---|
| Initiator Charge | |
| Deionized Water | 3.8 g |
| Sodium Persulfate (0.5%) | 1.17 g |
| Cook-Off Initiator #1 | |
| Deionized Water | 1.9 g |
| Ethanol | 1.9 g |
| Sodium Persulfate | 0.23 g |
| Cook off Initiator #2 | |
| Deionized Water | 1.9 g |
| Ethanol | 1.9 g |
| Sodium Persulfate | 0.23 g |
| Cook off Initiator #3 | |
| Deionized Water | 1.9 g |
| Ethanol | 1.9 g |
| Sodium Metabisulfite | 0.23 g |
| Total | 701.46 g |

Leaching Process 550 grams of the water insoluble copolymer prepared in accordance with Comparative Example 8 was transferred to the leaching vessel and the copolymer was subjected to a leaching process to remove unreacted monomer, as described below.

| First Leach | |
|---|---|
| Water added to precipitate polymer | 1100 g |
| Decant off effluent | 1361 g |
| Ethanol to redissolve | 100 g |
| Second Leach | |
| Water added to precipitate polymer | 1000 g |
| Decant off effluent | 1105 g |
| Ethanol to redissolve | 100 g |
| Third Leach | |
| Water added to precipitate polymer | 1000 g |
| Decant off effluent | 1271 g |
| Ethanol to redissolve | 125 g |

After completion of the leaching of the homopolymer of Comparative Example 8, the pH of 90 grams of the leached homopolymer was adjusted 9.7 with 0.28 grams of a 30% ammonium hydroxide solution. The pH adjusted homopolymer product was diluted to 5% TSC with water. Upon dilution, the homopolymer precipitated out of solution, indicating that it was insoluble in water. The leached and pH adjusted copolymer product synthesized in Comparative Example No. 8 exhibited the following properties:

| | |
|---|---|
| Viscosity, cPs | 1900 |
| % Solids content | 25.6% |
| % Ethanol | 16.5% |
| % Water | 57.9% |
| Residual monomers | |
| 2-Hydroxyethyl Methacrylate | <0.01% |
| 4-Hydroxybutyl acrylate | <0.01% |

COMPARATIVE EXAMPLE 9

A copolymer comprising 67 weight % 2-hydroxyethyl methacrylate and 33 weight % 4-hydroxybutyl acrylate was prepared in accordance with the following recipe:

| Recipe | |
|---|---|
| Reactor Charge | |
| 2-Hydroxyethyl Methacrylate (Mitsubishi) | 16.6 Kg |
| 4-Hydroxybutyl acrylate | 8.3 Kg |
| Ethanol | 24.1 Kg |
| Deionized Water | 24.1 Kg |
| Initiator Charge | |
| Deionized Water | 0.4 Kg |
| Sodium Persulfate (0.5%) | 0.13 Kg |
| Cook-Off Initiator #1 | |
| Deionized Water | 0.2 Kg |
| Ethanol | 0.2 Kg |
| Sodium Persulfate | 0.025 Kg |
| Cook off Initiator #2 | |
| Deionized Water | 0.2 Kg |
| Ethanol | 0.2 Kg |
| Sodium Persulfate | 0.025 Kg |
| Cook off Initiator #3 | |
| Deionized Water | 0.2 Kg |
| Ethanol | 0.2 Kg |
| Sodium Persulfate (Metabisulfite) | 0.025 Kg |
| Total | 75 Kg |

Leaching Process 75 kilograms of the water insoluble copolymer prepared in accordance with Comparative Example 9 was transferred to the leaching vessel and the copolymer was subjected to a leaching process to remove unreacted monomer is described below.

| | |
|---|---|
| First Leach | |
| Water to precipitate polymer | 94.1 Kg |
| Decant off effluent | 93.3 Kg |
| Ethanol to redissolve | 7.5 Kg |
| Second Leach | |
| Water to precipitate polymer | 74.8 Kg |
| Decant off effluent | 92.9 Kg |
| Ethanol to redissolve | 7.5 Kg |
| Third Leach | |
| Water to precipitate polymer | 74.8 Kg |
| Decant off effluent | 81.5 Kg |
| Ethanol to redissolve | 9.4 Kg |

After completion of the leaching of the copolymer product of Comparative Example 9, the pH of 90 grams of the leached copolymer adjusted with 0.022 grams of a 30% ammonium hydroxide solution. The pH was measured to be about 8.38. Upon visual inspection, the copolymer was clear in solution. The copolymer was then diluted to 5% TSC with water. Upon visual inspection, the diluted copolymer product of Comparative Example 9 appeared as a milky dispersion in solution. The leached and pH adjusted copolymer product synthesized in Comparative Example No. 9, above, exhibited the following properties:

| | |
|---|---|
| Viscosity, cPs | 660 |
| % Solids content | 23.6% |
| % Ethanol | 23.5% |
| % Water | 52.9% |
| Residual monomers | |
| 2-Hydroxyethyl Methacrylate | <50 ppm |
| 4-Hydroxybutyl acrylate | <10 ppm |

EXAMPLE 10

1625 grams of the leached, water insoluble copolymer prepared in accordance with Comparative Example 9 was transferred to the leaching vessel and the copolymer was subjected to an additional leaching process to replace the ethanol with propylene glycol, as described below.

| 2$^{nd}$ LEACHING PROCESS | |
|---|---|
| First Leach | |
| Water to precipitate polymer | 1625 g |
| Decant off effluent | 1999 g |
| Propylene glycol to redissolve | 150 g |
| Second Leach | |
| Water to precipitate polymer | 1625 g |
| Decant off effluent | 2048 g |
| Propylene glycol to redissolve | 100 g |
| Third Leach | |
| Water to precipitate polymer | 1625 g |
| Decant off effluent | 1788 g |
| Propylene glycol to redissolve | 100 g |

The leached copolymer product of Example 10 exhibited the following properties:

| | |
|---|---|
| Viscosity, cPs | 80,000 |
| pH | 3.2 |
| % Solids content | 29% |
| % Water | 59% |
| % Propylene glycol | 12% |
| % Ethanol | 0.3% |
| Residual monomers | |
| 2-Hydroxyethyl Methacrylate | 90 ppm |
| 4-Hydroxybutyl acrylate | 25 ppm |

EXAMPLE 11

A homopolymer of 2-hydroxyethyl methacrylate was prepared in accordance with the following recipe:

| Recipe | |
|---|---|
| Reactor Charge | |
| 2-Hydroxyethyl Methacrylate (Mitsubishi) | 24.96 Kg |
| Ethanol | 24.12 Kg |
| Deionized Water | 24.12 Kg |
| Initiator Charge | |
| Deionized Water | 0.41 Kg |
| Sodium Persulfate (0.5%) | 0.13 Kg |

-continued

| Recipe | | |
|---|---|---|
| Cook-Off Initiator #1 | | |
| Deionized Water | 0.2 | Kg |
| Ethanol | 0.2 | Kg |
| Sodium Persulfate | 0.025 | Kg |
| Cook off Initiator #2 | | |
| Deionized Water | 0.2 | Kg |
| Ethanol | 0.2 | Kg |
| Sodium Persulfate | 0.025 | Kg |
| Cook off Initiator #3 | | |
| Deionized Water | 0.2 | Kg |
| Ethanol | 0.2 | Kg |
| Sodium Metabisulfite | 0.025 | Kg |
| Total | 74.59 | Kg |
| % Solids Content | 34.7% | |

The was subjected to a leaching process to remove the residual unreacted 2-hydroxyethyl methacrylate monomer.

Leaching Process 75 kilograms of the water insoluble homopolymer prepared in accordance with Example 11 was transferred to the leaching vessel and the polymer was subject to a leaching process to remove unreacted monomer, as described below.

| First Leach | | |
|---|---|---|
| Water to precipitate polymer | 131.6 | Kg |
| Decant off effluent | 105.3 | Kg |
| Ethanol to redissolve | 8.5 | Kg |
| Second Leach | | |
| Water to precipitate polymer | 73.5 | Kg |
| Decant off effluent | 84.4 | Kg |
| Ethanol to redissolve | 7.8 | Kg |
| Third Leach | | |
| Water to precipitate polymer | 74.9 | Kg |
| Decant off effluent | 84.1 | Kg |
| Ethanol to redissolve | 9.4 | Kg |

$2^{nd}$ Leaching Process 1624 grams of leached polymer prepared in accordance with Example 11 was transferred to the leaching vessel and the polymer was subjected to a further leaching process to replace the ethanol with propylene glycol, as described below.

| First Leach | | |
|---|---|---|
| Water to precipitate polymer | 1624 | g |
| Decant off effluent | 2062 | g |
| Propylene glycol to redissolve | 154 | g |
| Second Leach | | |
| Water to precipitate polymer | 1624 | g |
| Decant off effluent | 1873 | g |
| Propylene glycol to redissolve | 108 | g |
| Third Leach | | |
| Water to precipitate polymer | 1624 | g |
| Decant off effluent | 1718 | g |
| Propylene glycol to redissolve | 103 | g |

The leached copolymer product synthesized in Example 11, above, exhibited the following properties:

| Viscosity, cPs | 540,000 |
|---|---|
| pH | 3.5 |
| % Solids content | 28% |
| % Water | 58% |
| % Propylene glycol | 14% |
| % Ethanol | 0.5% |
| Residual monomer | |
| 2-Hydroxyethyl Methacrylate | <10 ppm |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:

1. A method for the preparation of a gel-free, water insoluble, hydrophilic copolymer of 2-hydroxyethyl methacrylate, 4-hydroxybutyl acrylate and at least one of acrylic acid or methacrylic acid substantially in the absence of a chain transfer agent comprising:
   introducing monomeric 2-hydroxyethyl methacrylate, 4-hydroxybutyl acrylate and at least one of acrylic acid or methacrylic acid into a solution of water and alcohol, wherein the monomeric 2-hydroxyethyl methacrylate contains ethylene glycol dimethacrylate impurities up to about 0.15% by weight, based on the weight of the monomer; and
   copolymerizing the monomeric 2-hydroxyethyl methacrylate, 4-hydroxybutyl acrylate and at least one of acrylic acid or methacrylic acid to form a polymerization mixture.

2. The method of claim 1, wherein the monomeric 2-hydroxyethyl methacrylate contains ethylene glycol dimethacrylate impurities in the range of about 0.05% to about 0.1% by weight, based on the weight of the monomer.

3. The method of claim 1, wherein the monomeric 2-hydroxyethyl methacrylate contains impurities in a total amount of no more than about 3% by weight, based on the weight of the monomer, and wherein the impurities are selected from the group consisting of ethylene glycol dimethacrylate, diethylene glycol monomethacrylate, methacrylic acid and mixtures thereof.

4. The method of claim 1, further comprising leaching the copolymer of 2-hydroxyethyl methacrylate, 4-hydroxybutyl methacrylate and at least one of acrylic acid or methacrylic acid to substantially remove residual monomer.

5. The method of claim 4, wherein the polymerization mixture is leached and precipitated with water to substantially remove residual monomer.

6. The method of claim 5, wherein the copolymer precipitate is redissolved in a liquid selected from the group consisting of alcohols, alkylene glycols and polyalkylene glycols.

7. The method of claim 4, further comprising adjusting the pH of the polymerization mixture to a pH sufficient to render the copolymer water soluble.

8. The method of claim 7, comprising adjusting the pH of the polymerization mixture to a pH of greater than about 4.5.

9. The method of claim 8, wherein the pH of the polymerization mixture is adjusted to a pH of about 5.5 to about 7.5.

10. The method of claim 1, further comprising adding a polyalkylene glycol to the polymerization mixture and substantially removing the solution of alcohol and water, to form a hydrophilic pressure sensitive adhesive.

11. The method of claim 10, wherein the polyalkylene glycol is selected from the group consisting of polyethylene glycol, polypropylene glycol, copolymers of ethylene glycol and propylene glycol, and mixtures thereof.

12. The method of claim 11, wherein the polyalkylene glycol is polyethylene glycol.

13. The method of claim 4, further comprising adding a polyalkylene glycol to the polymerization mixture and substantially removing the solution of alcohol and water, to form a hydrophilic pressure sensitive adhesive.

14. The method of claim 13, wherein the polyalkylene glycol is selected from the group consisting of polyethylene glycol, polypropylene glycol, copolymers of ethylene glycol and propylene glycol, and mixtures thereof.

15. The method of claim 14, wherein the polyalkylene glycol is polyethylene glycol.

16. The method of claim 7, further comprising adding a polyalkylene glycol to the polymerization mixture and substantially removing the solution of alcohol and water, to form a hydrophilic pressure sensitive adhesive.

17. The method of claim 16, wherein the polyalkylene glycol is selected from the group consisting of polyethylene glycol, polypropylene glycol, copolymers of ethylene glycol and propylene glycol, and mixtures thereof.

18. The method of claim 17, wherein the polyalkylene glycol is polyethylene glycol.

19. The method of claim 1, further comprising adding a flexiblizing agent to the polymerization mixture and substantially removing the solution of alcohol and water, to form a flexible coating.

20. The method of claim 19, wherein the flexiblizing agent is selected from glycerin and propylene glycol.

21. The method of claim 4, further comprising adding a flexiblizing agent to the polymerization mixture and substantially removing the solution of alcohol and water, to form a flexible coating.

22. The method of claim 21, wherein the flexiblizing agent is selected from glycerin and propylene glycol.

23. The method of claim 7, further comprising adding a flexiblizing agent to the polymerization mixture and substantially removing the solution of alcohol and water, to form a flexible coating.

24. The method of claim 23, wherein the flexiblizing agent is selected from glycerin and propylene glycol.

* * * * *